United States Patent [19]

Baughman et al.

[11] 4,210,420
[45] Jul. 1, 1980

[54] DETECTION OF FIBRIN MONOMER AND COMPOSITION THEREFOR

[75] Inventors: D. Joe Baughman, Flemington; Ann Lytwyn, New Brunswick; Kurt Myrmel, Somerville, all of N.J.

[73] Assignee: Ortho Diagnostics Inc., Raritan, N.J.

[21] Appl. No.: 960,421

[22] Filed: Nov. 13, 1978

[51] Int. Cl.² .................... G01N 33/16; G01N 31/02; G01N 21/22
[52] U.S. Cl. .................................. 23/230 B; 252/408
[58] Field of Search ....................... 23/230 B; 252/408

[56] References Cited
U.S. PATENT DOCUMENTS

| 3,915,640 | 10/1975 | Turner | 23/230 B |
| 4,090,846 | 5/1978 | Buck | 424/12 X |

OTHER PUBLICATIONS

C. A. Vega et al., Anal. Chem., 48, (9), 1293–1296, (Aug. 1976).

Primary Examiner—Sidney Marantz
Attorney, Agent, or Firm—Ralph T. Lilore; Geoffrey G. Dellenbaugh

[57] ABSTRACT

A quantitative method and composition for precipitating fibrin monomers from plasma in the presence of fibrinogen, with only a small amount, if any, of fibrinogen being precipitated. A buffered precipitating agent is provided having a pH in the range of 6.5±0.5, the buffer being one having a pKa in the range of 6 to 7 and protamine sulfate at a level of 0.025 to 0.2% by weight. Suitable buffers are 2-(N-morpholino)ethanesulfonic acid, sodium phosphate, histidine, maleic acid and imidazole. Analysis of the amount of fibrin present can be made by analyzing for protein using preferably a basic urea solution containing sodium hydroxide and measuring the absorbance at 282 nanometers.

15 Claims, No Drawings

DETECTION OF FIBRIN MONOMER AND COMPOSITION THEREFOR

BACKGROUND OF THE INVENTION

The blood clotting process in normal individuals involves many intricate, complex steps including, in the final stages, the conversion of fibrinogen to fibrin monomer and subsequent polymerization to fibrin polymeric gel via the enzyme thrombin. It is generally accepted that prior to the formation of the clot, fibrin monomer combines with circulating fibrinogen to from soluble complexes. When the circulating fibrinogen concentration is insufficient to complex with the fibrin and therefore is insufficient to maintain the solubility of the fibrin monomer, the fibrin polymerizes and the clot is formed.

Ordinarily, in normal, healthy individuals there is no thrombin circulating in the blood, although there is some evidence to indicate that very small amounts of thrombin might from time to time be generated. Such amounts are usually insufficient to cause any significant intravascular coagulation. If some thrombin does happen to get generated as is normal in tissue injury at a wound for example, clots result from the action of the released thrombin. These clots are removed by the normal action of the body whereby plasmin dissolves the clot leaving small amounts of fibrin degradation products circulating in the bloodstream. Even if thrombin is present, it is likely that not all of the of the fibrin formed is converted to a clot in which case some free fibrin monomer is left circulating in the blood. So it can be seen that in normal individuals one would not be surprised to see some low level of fibrin monomer and fibrin degradation product circulating in the blood.

If, however, for some reason the coagulation system becomes abnormal in a way which results in larger amounts of thrombin than is normally encountered, then significant intravascular coagulation can occur. The coagulation process is of course accompanied by corresponding high concentrations of the soluble complexes of fibrin monomer and fibrinogen as indicated previously. The body attempts to remove the fibrin monomer - fibrinogen complex via the plasmin route as fast as it is being formed via the thrombin route. When thrombin levels are too high however, the thrombin mediated reaction overwhelms the plasmin reaction leaving fibrin monomer clearly discernible in the blood. Therefore, the concentration of fibrin monomer present is a measure of how abnormally high the thrombin level is and therefore and indication of the tendency of the patient toward intravascular coagulation. Since direct measurements of thrombin are not usually possible (the enzyme is rapidly removed by circulating inhibitors) it is very desirable to measure the fibrin monomers formed.

Unfortunately, the detection of fibrin monomers has not been readily achieved in the prior art due, at lease in part, to the fact that attempts to precipitate low levels of monomers with protamine sulfate have also caused the precipitation of fibrinogen. Fibrinogen precipitates as a white flocculent material easily distinguishable from the gel or strands formed from fibrin monomers. It is difficult at low concentrations to clearly identify the fibrin gel in the presence of the flocculent fibrinogen precipitate, however.

In view of this, the early detection of intravascular coagulation is somewhat uncertain when presently available test methods are relied upon. Since effective use of therapy depends, to a large extent, on its initiation in the early stages prior to irreversible damage, early diagnosis of low levels of intravascular coagulation is critical.

PRIOR ART

Protamine sulfate has been reported as a precipitating agent for fibrin and fibrin degradation products. Representative of the literature are the following:

U.S. Pat. No. 3,915,640 discusses the use of protamine sulfate in a test composition for precipitating fibrin monomers or fibrin degradation products using finely divided colored particles as a medium to enhance the visualization of the precipitate. The conditions of the test are such that the pH of the protamine sulfate solution is about 6.5 and the ionic strength of that system is about 0.15. This latter figure is derivable from the 0.85% by weight of sodium chloride used in the test composition. The test described in this patent is not run in the presence of a buffer however, and therefore, although the test reagent itself is at pH 6.5, the actual pH of the test is the pH of the test plasma usually 7.4 or higher. Therefore, the pH conditions of the test are uncontrolled and will vary with the pH of the tested plasma.

In "Effect of Protamine Sulphate on the Solubility of Fibrinogen, Its Derivatives and Other Plasma Proteins" by Z. S. Latallo, Z. Wegrzynowicz, A. Z. Budzynski and M. Kopec, Scand. J. Haem. Suppl. 13:151–162 (1971), a protamine sulfate system was described. The authors examined the effects of pH, salt concentrations, protamine sulfate concentration and temperature on fibrin monomer precipitation. They chose as optimum conditions a pH of 7.8, a protamine sulfate concentration between 0.1 and 0.2 percent, 0.15 M sodium chloride and 37° C. Under these conditions, while fibrin monomer precipitates, significant amounts of fibrinogen also precipitate giving at best a semiquantitative measure of the amount of fibrin present.

In "Detection of Intravascular Coagulation by a Serial-Dilution Protamine Sulfate Test" by Victor Gurewich, M.D., F.A.C.P., and Elizabeth Hutchinson, B.S., Boston, Massachusetts, Annals of Internal Medicine, Volume 75, Number 6, December 1971, pages 895–902, the authors describe a semi-quantitative protamine sulfate test using serial dilutions of protamine sulfate in tris buffer. The conditions used are similar to those in the Latallo et al, paper. The difference is that protamine sulfate is used at various dilutions (concentrations) and the dilution at which precipitation occurs is reported.

Other references which relate to the use of protamine sulfate are as follows:

"Incorporation of 125 I-Fibrinogen in Circulating Soluble Fibrin Monomer Complexes During Hypercoagulability" by R. von Hugo, R. Hafter, B. Stein, A. Stemberger, H. Rjosk and H. Graeff, Thrombosis Research Vol. 10, pp. 703–710, 1977, Pergamon Press, Ltd.

"Soluble Fibrin Complexes: Separation as a Function of pH and Characterization" by Y. Benabid, E. Concord and M. Suschillon, Thrombos Haemostas (Stuttg.) 1977, pp. 144–153.

"Correlation of The Serial-Dilution Protamine Sulfate Test with Models of Hypercoagulability and Thrombosis in Dogs" by P. Bailey Francis, M.D. and James E. Wilson, III, M.D., Sanfelippo MJ et al: Am J Clin Path 56:166–173, 1971.

SUMMARY OF THE INVENTION

The present invention presents a quantitative method and composition for precipitating fibrin monomer from plasma with only a small, if any, amount of fibrinogen being precipitated.

In accordance with the present invention, an aqueous sodium chloride solution having an ionic strength of 0.15 to 5.0 and preferably 0.3 to 0.35 and a pH of 6.5±0.5 together with a buffering amount of a buffer having a pKa in the range of 6 to 7 and preferably 6.5 and an amount of protamine sulfate at a level of 0.025 to 0.2% by weight and preferably 0.08% to 0.15% weight is provided.

Suitable buffers are 2-(N-morpholino)ethanesulfonic acid, sodium phosphate, histidine, maleic acid and imidazole.

The actual buffer used is not critical however, as long as it is substantially inert with respect to the components of the system and has a pKa in the range recited. Those skilled in the art may select any comparable buffer for use herein.

The protamine sulfate is preferably used in the form of an aqueous solution preferably containing 1% by weight of protamine sulfate and is added when appropriate to the correct concentration as indicated above.

In carrying out the method of the present invention, the above described precipitating composition is added to preferably freshly drawn anti-coagulated plasma and the mixture allowed to incubate preferably at room temperature (instead of 37° C. which is required in Latallo's method). A precipitate forms which contains essentially all of the fibrin monomer present in the plasma sample and only insignificant amounts of fibrinogen.

At this point, the presence of the precipitate is qualitative evidence of the presence of fibrin monomer and to the extent that it exceeds normal levels in presumptive qualitative evidence of intravascular coagulation. As an added aspect of the invention, however, it is possible to quantify the level of fibrin monomer by analyzing the precipitate for protein and comparing the value obtained with that obtained on a known sample of fibrin, a standard, or on a "normal" sample. It is the very specific precipitating quality of the present composition which permits the protein analysis to be correlated with fibrin monomer presence.

While there are many techniques known in the art for conducting the protein analysis, the present invention preferably provides dissolving the precipitate in a denaturing solvent such as guanidine hydrochloride, basic urea and the like and measuring protein by absorption of ultra violet light.

Preferred is a basic urea solution, and preferably a solution of urea containing sodium hydroxide (40% urea and 0.2 N NaOH). The solution is then submitted to absorbance measurements at 282 nanometers (after approximate corrections for scatter) and compared to blanks and controls. For example, known solutions of fibrin can be prepared and used as abnormal and normal controls against which the unknowns are tested. The amount of fibrin in the plasma of a statistically significant number of normal subjects can also be established and a range of concentrations developed to designate normal levels of fibrin monomer. Abnormal samples will be those having fibrin monomer concentrations above the established normal range.

Other methods of assaying for protein such as gravimetric or colorimetric techniques can be employed as well as the absorbance method but the latter is preferred because of its simplicity.

The present invention then, it can be seen, presents a quantitative method for distinguishing between plasmas having abnormal levels of fibrin present and those having normal levels of fibrin present with little or no interference from fibrinogen. It also permits the use of room temperature addition and incubation of protamine sulfate with plasma whereas the prior art method requires a 37° C. incubation.

The following examples are given to illustrate specific embodiments of the invention:

EXAMPLE 1

Preparation of a Buffer Solution 9.76 grams of 2-(N-morpholino)ethanesulfonic acid (MES) and 300 ml of 1 N sodium hydroxide solution are dissolved in a total volume of 1 liter with distilled water resulting in a solution (Solution A) which is 0.05 molar MES, and 0.3 molar sodium hydroxide and having an ionic strength of 0.3. A second solution (Solution B) is made up in which 9.76 grams of MES and 16.53 grams of sodium chloride are dissolved in a total volume of 1 liter of distilled water. This solution is 0.05 molar MES and contains sodium chloride at an ionic strength of 0.3. The two above solutions are mixed together in proportions such that the final pH if 6.5. The ionic strength remains at 0.3.

Using the above procedure and varying the amounts of sodium hydroxide and sodium chloride added to the solutions, a range of ionic strengths from 0.15 to 5.0 can be obtained. For example, when 350 ml of 1 N sodium hydroxide is used in solution A and 20.46 grams of sodium chloride is used in the preparation of solution B, both solutions are 0.35 molar and when mixed in equal proportions to give a pH of 6.5, the ionic strength of the final solution remains at 0.35.

Similarly, other values within the range can be prepared using the appropriate compositions.

EXAMPLE 2

The method of the present invention is preferably carried out using the following procedure:

To 1.8 ml of the first combined buffer solution of Example 1 is added 0.2 ml of an aqueous solution containing protamine sulfate at a concentration of 10 milligrams per milliliter. This results in a solution which can be used for detecting fibrin in accordance with the present invention. The level of protamine sulfate used in this solution is sufficient to precipitate amounts of fibrin which would otherwise remain in the solution.

EXAMPLE 3

This example is presented to show the utilization of the protamine sulfate buffer solution of the present invention in detecting the presence of fibrin. Freshly drawn citrated plasma (0.2 ml) is added to 2 ml of the test solution obtained in Example 2. This mixture is allowed to sit at room temperature for 30 minutes. After 30 minutes the tube is centrifuged 15 minutes at approximately 3,000×G. The assay system of the invention permits the precipitation at this point of a complex containing essentially all of the fibrin that was present in the plasma sample. The supernatant contains the major portion of the fibrinogen originally present in the plasma sample. The precipitate is collected and assayed using an absorbance technique described as follows:

The supernatant is discarded and the tube is allowed to drain thoroughly. The precipitate is washed with 2 ml of 0.9% sodium chloride and centrifuged a second time under the above conditions. After the second centrifugation, the precipitate is dissolved in 1 ml of an aqueous solution containing 40% urea and 0.2 molar sodium hydroxide. The absorbance of the solution thus obtained was measured at 282 nanometers corrected for scatter at 320 nanometers and corrected for the appropriate blank. The absorbance at 282 nanometers when corrected was 0.048 (0.054 on a duplicate run). This absorbance is equivalent to a fibrin concentration of 15.8 mg/dl.

EXAMPLE 4

The procedure of Example 1 is followed using the following solutions A&B in the preparation of a buffer solution.

A.

6.9 gms. $NaH_2PO_4$—$H_2O$
14.61 gms. NaCl
Q.S. to 1 liter with distilled water

B.

13.4 gms. $Na_2HPO_4$—7 $H_2$
8.77 gms. NaCl
Q.S. to 1 liter with distilled water These solutions are mixed until the appropriate pH (6.5±0.05) is reached in accordance with the procedure set forth in Example 1.

What is claimed is:

1. A fibrin monomer precipitating composition comprising water, sodium chloride, protamine sulfate, a buffering amount of a buffer having a pKa in the range of 6 to 7, said composition having a pH of 6.5±0.5 and an ionic strength of 0.15 to 5.0.

2. The composition of claim 1 wherein the ionic strength is 0.3 to 0.35.

3. The composition of claim 2 wherein the protamine sulfate is present at a level of 0.025 to 0.2% by weight.

4. The composition of claim 3 wherein the buffer is 2-(N-morpholino)ethanesulfonic acid, sodium phosphate, histidine, maleic acid or imidazole.

5. The composition of claim 3 wherein the buffer is 2-(N-morpholino)ethanesulfonic acid.

6. A method for the determination of fibrin monomer in plasma which comprises contacting plasma with the composition of claim 1 to form a precipitate, analyzing the precipitate for a determination of its protein content and comparing the value for the amount of protein obtained with that obtained on a sample containing a known amount of fibrin monomer.

7. The method of claim 6 wherein the precipitate is analyzed for protein by dissolving it in a denaturing solvent and measuring the absorbance of the solution at 282 nanometers.

8. The method of claim 7 wherein the composition of claim 5 is used as the precipitation composition.

9. The method of claim 8 wherein the precipitate is dissolved in an aqueous basic urea solution.

10. The method of claim 9 wherein the aqueous basic urea composition comprises sodium hydroxide.

11. A method for the determination of fibrin monomer in plasma which comprises contacting plasma with protamine sulfate in the presence of water, sodium chloride, a buffering amount of a buffer having a pka in the range of 6 to 7, at a pH of 6.5±0.5 and an ionic strength of 0.15 to 5.0 to form a precipitate, analyzing the precipitate for a determination of its protein content and comparing the value for the amount of protein obtained with that obtained on a sample containing a known amount of fibrin monomer.

12. The method of claim 11 wherein the precipitate is analyzed for protein by dissolving it in a denaturing solvent and measuring the absorbance of the solution at 282 nanometers.

13. The method of claim 12 wherein the buffer is 2-(N-morpholino)ethanesulfonic acid.

14. The method of claim 13 wherein the precipitate is dissolved in an aqueous basic urea solution.

15. The method of claim 14 wherein the aqueous basic urea composition comprises sodium hydroxide.

* * * * *